United States Patent [19]

Chen

[11] Patent Number: 5,133,775

[45] Date of Patent: Jul. 28, 1992

[54] COVERING DEVICE FOR AN ARTIFICIAL LIMB

[76] Inventor: Sen-Jung Chen, No. 236, Sec. 3, Ho-Ping W. Rd., Taipei City, Taiwan

[21] Appl. No.: 693,951

[22] Filed: Apr. 29, 1991

[51] Int. Cl.⁵ .......................... A61F 2/54; A61F 2/60; A61F 2/78

[52] U.S. Cl. ...................................... 623/27; 623/57; 2/16; 2/22

[58] Field of Search .................. 623/27, 33, 38, 57, 623/32; 128/165; 2/61, 269-270, 16, 22

[56] References Cited

U.S. PATENT DOCUMENTS

| 403,783 | 5/1889 | Smart | 2/16 |
| 4,090,508 | 5/1978 | Gaylord | 128/165 X |
| 4,176,665 | 12/1979 | Terpening | 128/165 |
| 4,811,727 | 3/1989 | Etienne | 128/165 X |
| 4,846,843 | 7/1989 | Gammer | 623/57 |

FOREIGN PATENT DOCUMENTS

| 2067074 | 7/1981 | United Kingdom | 623/27 |
| 211833 | 7/1983 | United Kingdom | 128/165 |

*Primary Examiner*—Randall L. Green
*Assistant Examiner*—D. Willse
*Attorney, Agent, or Firm*—Ladas & Parry

[57] ABSTRACT

A covering device for a jointed artificial limb includes a covering layer covering the artificial limb. The covering layer can be made of semirigid PU foam. The covering layer has a screen-like flexible portion adjacent to the joint of the artificial limb. The flexible portion includes a plurality of slits.

2 Claims, 5 Drawing Sheets

COVERING DEVICE FOR AN ARTIFICIAL LIMB

FIELD OF THE INVENTION

The invention relates to a covering device, more particularly to a covering device for an artificial limb.

DESCRIPTION OF THE RELATED ART

Referring to FIG. 1, a conventional covering device for an artificial leg (A) includes a rectangular covering layer (B) covering the artificial leg (A) The rectangular covering layer (B) is cut and machined to form the leg-shaped covering layer (B'). The artificial leg (A), made of metal, has a knee (A1). The covering layer (B') is made of flexible polyurethane (hereinafter "PU") foam, a material which water easily penetrates through its large pores As a result, the covering layer (B') on the artificial leg (A) gradually gets water-logged and musty, and the artificial leg (A) can be easily damaged by rust. The knee (A1) of the artificial leg (A) severely suffers from rust damage, which adversely affects the bending effect of the knee (A1).

SUMMARY OF THE INVENTION

Therefore, the objective of the present invention is to provide an improved covering device for an artificial limb. The covering device, which may be made of semirigid PU foam, is waterproof. The covering device further includes a screen-like flexible portion comprised of a plurality of slits adjacent to the joint of the artificial limb so the artificial limb can bend freely.

Accordingly, this invention is a covering device for a jointed artificial limb. The covering device includes a covering layer covering the artificial limb. The covering layer can be made of semirigid PU foam. The covering layer has a screen-like flexible portion adjacent to the joint of the artificial limb. The flexible portion includes a plurality of slits.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
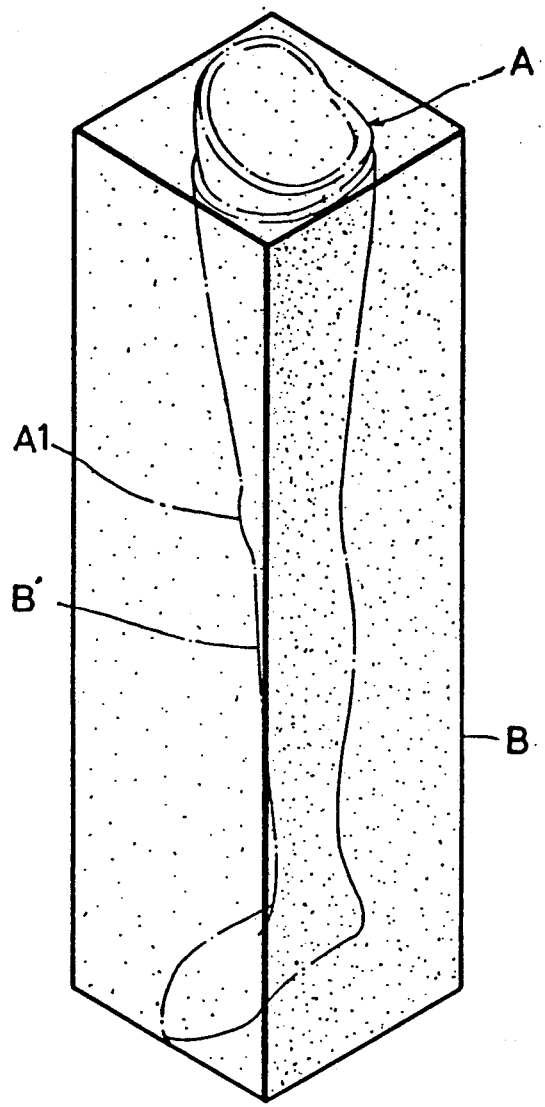
FIG. 1 is a schematic view of a conventional covering device covering an artificial leg.
Figure 2:
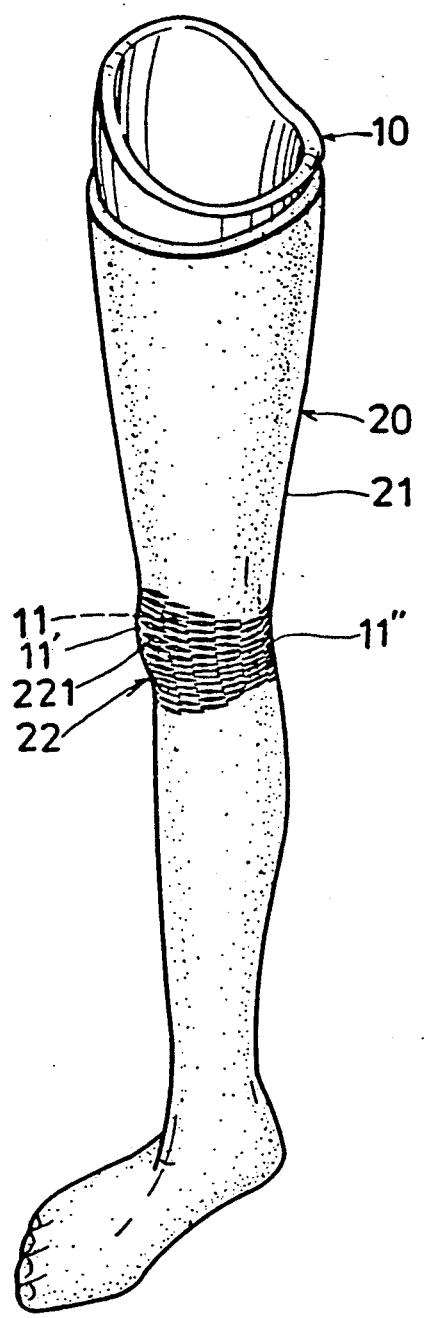
FIG. 2 is a perspective view of a preferred embodiment of a covering device of this invention for an artificial leg.
Figure 3:
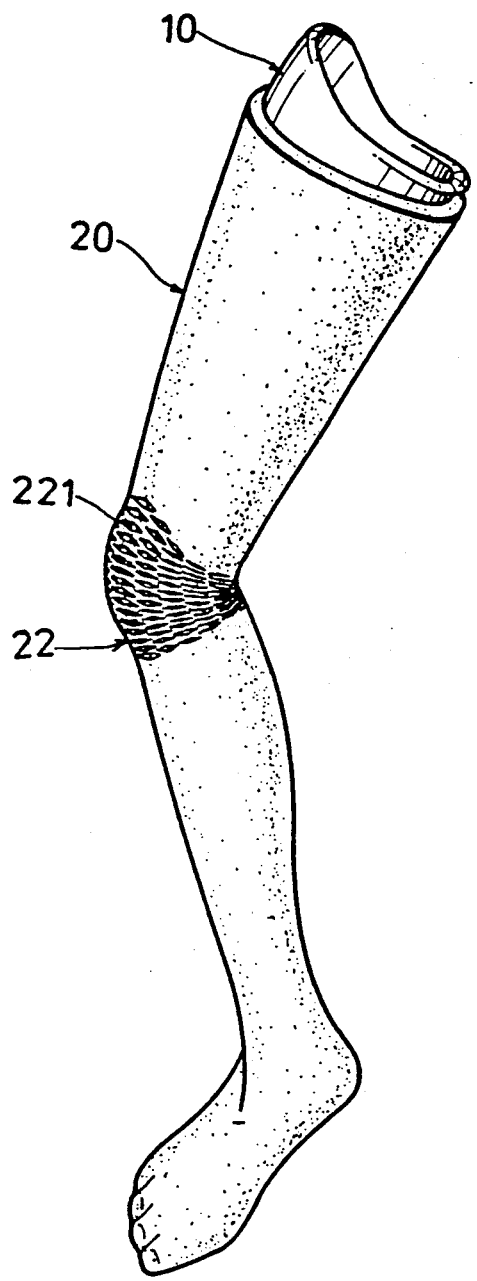
FIG. 3 is a perspective view of the covering device for an artificial leg in FIG. 2 when the artificial leg bends.
Figure 4:
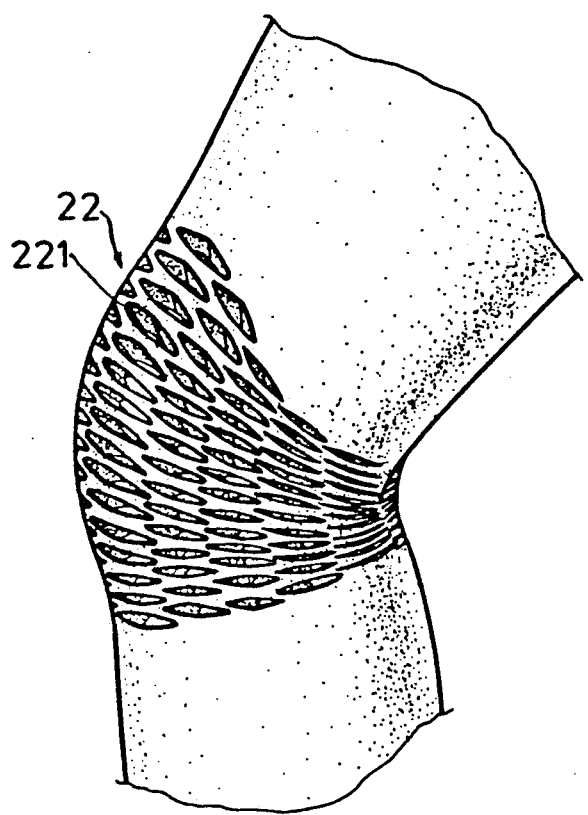
FIG. 4 is a schematic view of the screen-like flexible portion of the covering device for the artificial leg in FIG. 2.

Referring to FIGS. 2-4 a covering device 20 for an artificial leg 10 is shown. The covering device 20 of this invention includes a leg-shaped covering layer 21 integrally covering the artificial leg 10. The covering layer 21 is made of semirigid PU foam, which has smaller pores than the conventional covering layer described above. Water cannot easily penetrate the smaller pores on the covering layer 21, so the covering layer 21 has an waterproof effect. Therefore, the covering layer 21 and the artificial leg 10 cannot suffer from the disadvantages explained above.

The covering layer 21 includes a screen-like flexible portion 22 adjacent to and around the knee 11 of the artificial leg 10. The flexible portion 22 is widened at the front 11' and the back 11" of the knee 11. The flexible portion 22 includes a plurality of rhombic slits 221. The rhombic slits 221 are spaced apart from one another and are arranged in columns and rows. The longer diagonal of each rhombic slit 221 lies in a substantially horizontal position. When the artificial leg 10 bends, the rhombic slits 221 of the flexible portion 22 cooperatively expand and contract to effectuate the bending, so the artificial leg 10 can bend freely.

Figure 5:
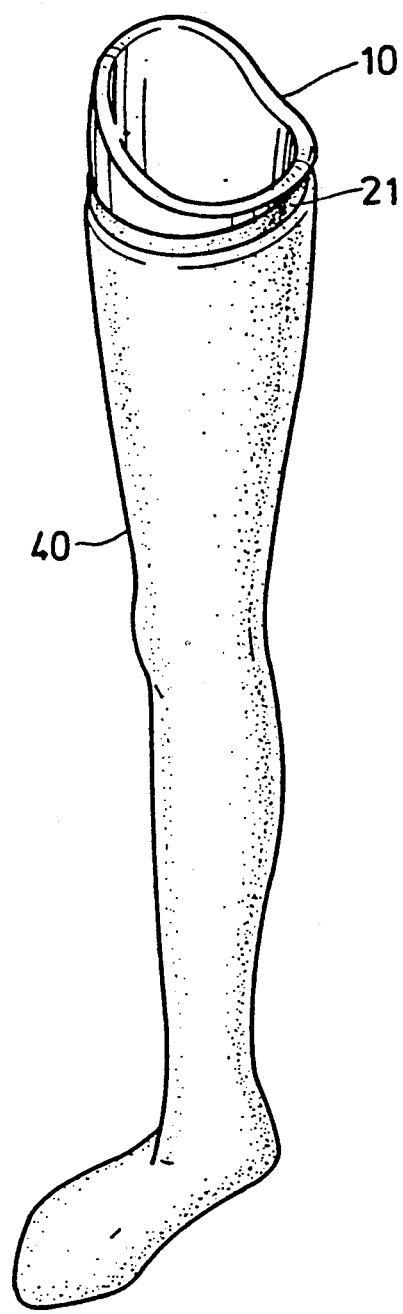
FIG. 5 shows that the covering device is sleeved in a cosmetic stocking.

FIG. 5 shows that the covering layer 21 on the artificial leg 10 is sleeved in a cosmetic stocking 40 for decoration.

While the present invention has been described in connection with what is considered the most practical and preferred embodiment, it is understood that this invention is not limited to the disclosed embodiment, but is intended to cover various arrangements included within the spirit and scope of the broadest interpretations and equivalent arrangements.

I claim:

1. A covering device for an artificial limb which has a joint, said covering device comprising:

a covering layer covering said artificial limb, said covering layer made of semirigid polyurethane foam;

said covering layer having a screen-like flexible portion adjacent to said joint of said artificial limb, said flexible portion having a plurality of slits formed thereon, said slits are rhombic-shaped and spaced apart from one another and are arranged in columns and rows.

2. The covering device of claim 1, wherein the rhombic-shaped slits have an axis and said axis lies in a substantially horizontal position.

* * * * *